(12) United States Patent
Kim et al.

(10) Patent No.: US 11,746,079 B2
(45) Date of Patent: Sep. 5, 2023

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Jeong Ju Moon, Daejeon (KR); Seok Ho Jeong, Daejeon (KR); Yun Ki Cho, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 204 days.

(21) Appl. No.: 17/040,784

(22) PCT Filed: Jun. 3, 2019

(86) PCT No.: PCT/KR2019/006637
§ 371 (c)(1),
(2) Date: Sep. 23, 2020

(87) PCT Pub. No.: WO2019/240417
PCT Pub. Date: Dec. 19, 2019

(65) Prior Publication Data
US 2021/0002204 A1    Jan. 7, 2021

(30) Foreign Application Priority Data
Jun. 11, 2018  (KR) ............. 10-2018-0067038
May 30, 2019  (KR) ............. 10-2019-0063854

(51) Int. Cl.
C07C 69/75    (2006.01)
C07D 303/42   (2006.01)
C07C 69/704   (2006.01)
C08K 5/00     (2006.01)

(52) U.S. Cl.
CPC ............ C07C 69/75 (2013.01); C07C 69/704 (2013.01); C07D 303/42 (2013.01); C08K 5/0016 (2013.01)

(58) Field of Classification Search
CPC ..... C07C 69/75; C07C 69/704; C07D 303/42; C06D 303/42; C08K 5/0016; C08K 5/11; C08K 5/12; C08K 5/1515; C08L 27/06
USPC ........................................................ 524/321
See application file for complete search history.

(56) References Cited

U.S. PATENT DOCUMENTS

| 10,717,846 B2* | 7/2020 | Kim | .............. C08L 23/12 |
| 10,844,194 B2* | 11/2020 | Kim | .............. C08L 27/06 |
| 11,186,702 B2* | 11/2021 | Kim | .............. C08K 9/04 |
| 2014/0309345 A1 | 10/2014 | Frenkel et al. | |
| 2015/0368431 A1 | 12/2015 | Ghosh-Dastidar et al. | |
| 2018/0163018 A1 | 6/2018 | Kim et al. | |
| 2018/0171103 A1 | 6/2018 | Kim et al. | |
| 2018/0319953 A1 | 11/2018 | Kim et al. | |
| 2019/0047938 A1 | 2/2019 | Kim et al. | |
| 2019/0248984 A1 | 8/2019 | Kim et al. | |

FOREIGN PATENT DOCUMENTS

| EP | 3211029 A1 | 8/2017 |
| EP | 3255086 A1 | 12/2017 |
| EP | 3434721 A1 | 1/2019 |
| JP | 2016-022708 | 2/2016 |
| KR | 10-2014-0116371 | 10/2014 |
| KR | 10-2015-0131016 | 11/2015 |

(Continued)

OTHER PUBLICATIONS

Summers, J.W., "Vinyl Chloride Polymers," Kirk-Othmer Enc. Chem. Technol., John Wiley & Sons. (Year: 2006).*

(Continued)

Primary Examiner — Frances Tischler
(74) Attorney, Agent, or Firm — Bryan Cave Leighton Paisner LLP

(57) ABSTRACT

Provided is a plasticizer composition, comprising: a cyclohexane-1,4-diester-based substance of the following Chemical Formula 1; an epoxidized alkyl ester composition comprising one or more compounds of the following Chemical Formula 2; and a citrate-based substance of the following Chemical Formula 3:

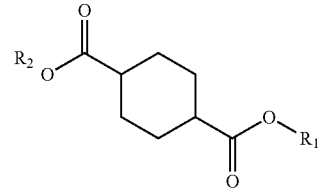

Chemical Formula 1

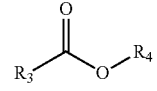

Chemical Formula 2

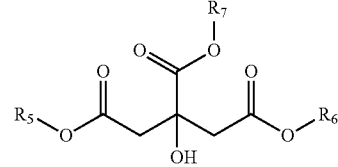

Chemical Formula 3 wherein in Chemical Formula 1 to Chemical Formula 3;
$R_1$ and $R_2$ each independently are a C8 alkyl group;
$R_3$ is a C8 to C20 alkyl group comprising one or more epoxy groups; and
$R_4$ to $R_7$ each independently are a C4 to C10 alkyl group.

11 Claims, No Drawings

(56) References Cited

FOREIGN PATENT DOCUMENTS

| KR | 10-2016-0047221 | 5/2016 |
| KR | 10-2016-0095875 | 8/2016 |
| KR | 10-2016-0112443 | 9/2016 |
| KR | 10-2017-0121059 | 11/2017 |
| KR | 10-2017-0141599 | 12/2017 |
| KR | 10-2018-0028035 A | 3/2018 |
| TW | 201815930 A | 5/2018 |
| WO | 2017-183876 A1 | 10/2017 |
| WO | 2018-110923 A1 | 6/2018 |

OTHER PUBLICATIONS

Database WPI Week 201776 Thomson Scientific, London, GB; AN 2017-730962 (3 Pages).
Database WPI Week 201846 Thomson Scientific, London, GB; AN 2018-494811 XP002803331 (3 Pages).

* cited by examiner

PLASTICIZER COMPOSITION AND RESIN COMPOSITION INCLUDING THE SAME

CROSS-REFERENCE TO RELATED APPLICATIONS

This application is a National Stage Application of International Application No. PCT/KR2019/006637 filed on Jun. 3, 2019, which claims priority to and the benefit of Korean Patent Application No. 10-2018-0067038, filed on Jun. 11, 2018, and Korean Patent Application No. 10-2019-0063854, filed on May 30, 2019, the disclosures of which are incorporated herein by reference in their entirety.

TECHNICAL FIELD

The present invention relates to a plasticizer composition and a resin composition including the same, and more particularly, to a plasticizer composition that is environmentally friendly and has high stability and excellent basic properties and a resin composition including the same.

BACKGROUND

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

Meanwhile, in compound industries requiring high heat resistance and low volatile loss as main desired physical properties, suitable plasticizers need to be used in consideration of the desired physical properties. In the case of polyvinyl chloride (PVC) compounds used for electric wires and cables, a PVC resin is mixed in combination with a third substance such as a plasticizer, a stabilizer, a pigment, or the like depending on properties required for corresponding specifications, such as tensile strength, an elongation rate, plasticization efficiency, volatile loss, tensile and elongation retention, and the like.

In various types of extrusion, injection, calendering, and compound industries relating to electric wires, flooring materials, automotive interior materials, films, hoses, tubes, and the like, general purpose phthalate products such as diisononyl phthalate (DINP), diisodecyl phthalate (DIDP), and the like are commonly used.

However, since these phthalate products are substances whose use is regulated or needs to be regulated depending on the purpose of the products, in order to satisfy market demand, general purpose non-phthalate products such as di(2-ethylhexyl) terephthalate (DOTP or DEHTP) and the like have been used, but an improvement in quality thereof is required.

In accordance with these environmental issues and demands for improvement in quality at a level equal to or higher than that of existing products, there is a need to develop a new product capable of improving the quality of existing products while having environmental friendliness. For this, there is ongoing research on development of a novel plasticizer composition that has superior physical properties to existing products and is environmentally friendly in order to ensure a vinyl chloride-based resin composition which is free from environmental issues and has excellent quality.

DISCLOSURE

Technical Problem

The present invention has been made in view of the above problems of the prior art, and is directed to providing a plasticizer composition that, when used as a plasticizer for a resin composition, is capable of enhancing physical properties such as plasticization efficiency, volatile loss, light resistance, thermal stability, migration, and the like at a superior level, and a resin composition including the same.

Technical Solution

One aspect of the present invention provides a plasticizer composition including: a cyclohexane-1,4-diester-based substance of the following Chemical Formula 1; an epoxidized alkyl ester composition including one or more compounds of the following Chemical Formula 2; and a citrate-based substance of the following Chemical Formula 3:

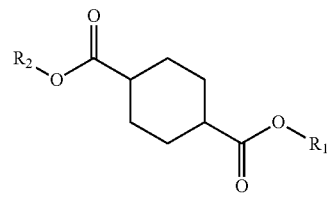

Chemical Formula 1

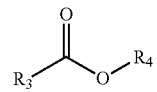

Chemical Formula 2

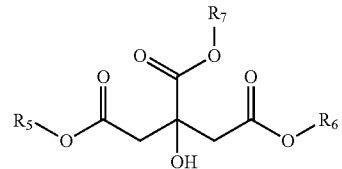

Chemical Formula 3 wherein in Chemical Formula 1 to Chemical Formula 3:
$R_1$ and $R_2$ each independently are a C8 alkyl group;
$R_3$ is a C8 to C20 alkyl group including one or more epoxy groups; and
$R_4$ to $R_7$ each independently are a C4 to C10 alkyl group.

Another aspect of the present invention provides a resin composition including: a resin in an amount of 100 parts by weight; and the above-described plasticizer composition in an amount of 5 to 150 parts by weight.

Advantageous Effects

A plasticizer composition according to an embodiment of the present invention is capable of improving physical properties such as plasticization efficiency, volatile loss, light resistance, heat resistance, and the like at a superior level when used in a resin composition.

DETAILED DESCRIPTION

Hereinafter, the present invention will be described in more detail to facilitate understanding of the present invention.

Terms and words used in this specification and claims should not be interpreted as being limited to commonly used meanings or meanings in dictionaries, and, based on the principle that the inventors can appropriately define concepts of terms in order to describe their invention in the best way, the terms and words should be interpreted with meanings and concepts which are consistent with the technological spirit of the present invention.

The names of compounds used in this specification can be generic names and are named according to the substituents which are characteristically bonded to each compound. Even though the name of the compound does not correspond to the generic name, it can be understood that it is named according to the substituent in the structure of the chemical formula.

As used herein, the term "alkyl group" can be understood to be linear or branched without other limitations other than a limitation in carbon number unless specifically mentioned otherwise.

In the present invention, an iodine value can be measured in accordance with ASTM D5768-02.

In the present invention, an oxirane content can be measured in accordance with ASTM D1652-04.

As used herein, the term "straight vinyl chloride polymer" is one kind of vinyl chloride polymer, can be polymerized through suspension polymerization, bulk polymerization, or the like, and refers to a polymer which is in the form of a porous particle in which a large amount of pores with a size of several tens to several hundreds of micrometers are distributed and has no cohesion and excellent flowability.

As used herein, the term "paste vinyl chloride polymer" is one kind of vinyl chloride polymer, can be polymerized through microsuspension polymerization, microseed polymerization, emulsion polymerization, or the like, and refers to a polymer which is in the form of a fine, compact, and non-porous particle with a size of several tens to several thousands of nanometers and has cohesion and poor flowability.

The terms "comprising", "including", "having", and derivatives thereof are not intended to exclude the presence of any additional components, steps, or procedures, whether they are specifically disclosed or not. To avoid any uncertainty, all compositions claimed through the use of the terms "comprising" and "including", whether polymers or otherwise, can include any additional additives, adjuvants, or compounds unless otherwise stated. In contrast, the term "consisting essentially of" excludes any other component, step, or procedure from the scope of any subsequent description, and excludes those that are not essential to operability. The terms "consisting of" excludes any element, step, or procedure that is not specifically described or listed.

1. Plasticizer Composition

A plasticizer composition according to an embodiment of the present invention includes: 1) a cyclohexane-1,4-diester-based substance of the following Chemical Formula 1; 2) an epoxidized alkyl ester composition including one or more compounds of the following Chemical Formula 2; and 3) a citrate-based substance of the following Chemical Formula 3:

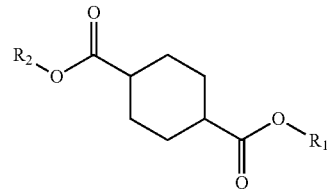

Chemical Formula 1

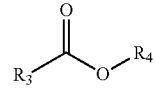

Chemical Formula 2

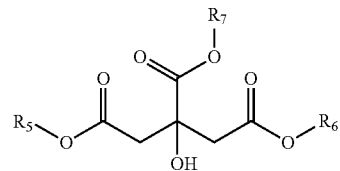

Chemical Formula 3 wherein in Chemical Formula 1 to Chemical Formula 3:

$R_1$ and $R_2$ each independently are a C8 alkyl group;

$R_3$ is a C8 to C20 alkyl group including one or more epoxy groups; and $R_4$ to $R_7$ each independently are a C4 to C10 alkyl group.

Hereinafter, each component of the plasticizer composition according to an embodiment of the present invention will be described in detail.

1) Cyclohexane-1,4-Diester-Based Substance

The cyclohexane-1,4-diester-based substance has a structure of Chemical Formula 1 and can impart environmental friendliness and excellent stability to the plasticizer composition. In addition, it can improve processing properties, such as plasticization efficiency, light resistance, an absorption rate, and the like, of the plasticizer composition.

Unless ester groups are bound to 1- and 4-positions of carbons of cyclohexane, plasticization efficiency, volatile loss, and the like are degraded.

When $R_1$ and $R_2$ in Chemical Formula 1 are alkyl groups having 9 or more carbon atoms, plasticization efficiency, migration, and the like are degraded, and when $R_1$ and $R_2$ are alkyl groups having 7 or less carbon atoms, volatile loss is significantly degraded, and thus an amount of volatilized components are increased in processing with a resin, which can cause air pollution problems.

$R_1$ and $R_2$ in Chemical Formula 1 can each independently be any one selected from the group consisting of an n-octyl group, an isooctyl group, and a 2-ethylhexyl group, and can be the same or different from each other.

The cyclohexane-1,4-diester-based substance can be dioctyl cyclohexane-1,4-dicarboxylate or di(2-ethylhexyl) cyclohexane-1,4-dicarboxylate.

The cyclohexane-1,4-diester-based substance can be included in an amount of 10 to 90 wt %, 20 to 90 wt %, or 30 to 80 wt % with respect to the total weight of the plasticizer composition, with the range of 30 to 80 wt % being preferred. When the above-described condition is satisfied, a resin composition which is favorable in terms of plasticization efficiency, volatile loss, light resistance, and mechanical properties such as tensile strength, an elongation rate, and the like can be provided.

When the cyclohexane-1,4-diester-based substance is directly prepared, direct esterification or trans-esterification of cyclohexane-1,4-dicarboxylic acid or a derivative thereof with an alcohol can be performed.

The derivative of the cyclohexane-1,4-dicarboxylic acid can be one or more selected from the group consisting of an anhydride of cyclohexane-1,4-dicarboxylic acid and an alkyl ester of cyclohexane-1,4-dicarboxylic acid. The alkyl ester can be a C1 to C6 alkyl ester.

The alcohol can be a C8 alkyl alcohol.

When the cyclohexane-1,4-diester-based substance of Chemical Formula 1 is prepared by direct esterification, the alcohol can be used in an amount of 2 to 10 moles, 2 to 8 moles, 2 to 6 moles, or 2 to 5 moles with respect to 1 mole of the cyclohexane-1,4-dicarboxylic acid or the derivative thereof, with the range of 2 to 5 moles being preferred.

The direct esterification can be performed in the presence of a catalyst, and the catalyst can be one or more selected from the group consisting of an inorganic acid, an organic acid, and a Lewis acid.

The inorganic acid can be one or more selected from the group consisting of sulfuric acid, hydrochloric acid, and phosphoric acid.

The organic acid can be one or more selected from the group consisting of p-toluenesulfonic acid, methanesulfonic acid, ethanesulfonic acid, propanesulfonic acid, butanesulfonic acid, and alkylsulfuric acid.

The Lewis acid can be one or more selected from the group consisting of aluminum derivatives (aluminum oxide, aluminum hydroxide), tin derivatives ($C_3$ to $C_{12}$ fatty acid tin, tin oxide, tin hydroxide), titanium derivatives ($C_3$ to $C_8$ tetraalkyl titanate, titanium oxide, titanium hydroxide), lead derivatives (lead oxide, lead hydroxide), and zinc derivatives (zinc oxide, zinc hydroxide).

When the catalyst is a homogeneous catalyst, the catalyst can be used in an amount of 0.01 to 5 parts by weight or 0.01 to 3 parts by weight with respect to 100 parts by weight of the sum of the cyclohexane-1,4-dicarboxylic acid or the derivative thereof and the alcohol, with the range of 0.01 to 3 parts by weight being preferred.

When the catalyst is a heterogeneous catalyst, the catalyst can be used in an amount of 5 to 200 parts by weight or 5 to 100 parts by weight with respect to 100 parts by weight of the sum of the cyclohexane-1,4-dicarboxylic acid or the derivative thereof and the alcohol, with the range of 5 to 200 parts by weight being preferred.

The direct esterification can be performed at 100 to 280° C., 130 to 250° C., or 150 to 230° C., with the range of 150 to 230° C. being preferred.

The direct esterification can be performed for 3 to 30 hours or 3 to 25 hours, with the range of 3 to 25 hours being preferred.

Meanwhile, when the cyclohexane-1,4-diester-based substance of Chemical Formula 1 is prepared by trans-esterification, trans-esterification of a derivative of cyclohexane-1, 4-dicarboxylic acid with an alcohol can be performed.

The derivative of cyclohexane-1,4-dicarboxylic acid can be an alkyl ester of cyclohexane-1,4-dicarboxylic acid, and methyl ester of cyclohexane-1,4-dicarboxylic acid is preferably used to facilitate the separation of a reaction product.

The alcohol can be used in an amount of 2 to 10 moles, 2 to 8 moles, 2 to 6 moles, or 2 to 5 moles with respect to 1 mole of the derivative of cyclohexane-1,4-dicarboxylic acid, with the range of 2 to 5 moles being preferred.

The trans-esterification can be performed in the presence of a catalyst, which provides an effect of reducing a reaction time.

The catalyst can be one or more selected from the group consisting of a Lewis acid and an alkali metal.

Descriptions of the Lewis acid are the same as the description on the direct esterification.

The alkali metal can be one or more selected from the group consisting of sodium alkoxide, potassium alkoxide, sodium hydroxide, and potassium hydroxide.

The catalyst can be used in an amount of 0.01 to 5 parts by weight or 0.01 to 3 parts by weight with respect to 100 parts by weight of the sum of the derivative of cyclohexane-1,4-dicarboxylic acid and the alcohol, with the range of 0.01 to 3 parts by weight being preferred.

The trans-esterification can be performed at 120 to 250° C., 135 to 230° C., or 140 to 220° C., with the range of 140 to 220° C. being preferred.

The trans-esterification can be performed for 0.5 to 10 hours or 0.5 to 8 hours, with the range of 0.5 to 8 hours being preferred.

In order to promote the discharge of water or a lower alcohol such as methanol and the like which is produced by the direct esterification or trans-esterification, one or more selected from the group consisting of benzene, toluene, xylene, and cyclohexane can be further added. In addition, for the same purpose, commercially available nitrogen or the like in an entrained form can be used.

The cyclohexane-1,4-diester-based substance prepared by direct esterification or trans-esterification can be purified by performing separate post-treatment. The post-treatment can be one or more selected from the group consisting of deactivation treatment (neutralization treatment, base treatment) of the catalyst, washing treatment, distillation treatment (decompression or dehydration treatment), and adsorption purification treatment.

Unlike the above-described preparation methods, a preparation method of preparing a cyclohexane-1,4-diester-based substance by hydrogenating a dialkyl terephthalate-based substance in the presence of a metallic catalyst can be used.

The hydrogenation is a reaction in which hydrogen is added in the presence of a metallic catalyst to eliminate the aromaticity of a benzene ring of a terephthalate and can be a kind of reduction reaction.

The hydrogenation is a reaction in which the terephthalate-based substance is reacted with hydrogen in the presence of a metallic catalyst to synthesize a cyclohexane-1,4-diester-based substance of Chemical Formula 1, and the hydrogenation conditions can include all the conventional hydrogenation conditions capable of hydrogenating only a benzene ring without affecting a carbonyl group substituted in benzene.

The hydrogenation can be performed by further including an organic solvent such as ethanol or the like, but the present invention is not limited thereto. The metallic catalyst can be a Rh catalyst, a Pt catalyst, a Pd catalyst, or the like, which is commonly used to hydrogenate a benzene ring, but the present invention is not limited thereto as long as it catalyzes a hydrogenation reaction as described above.

2) Epoxidized Alkyl Ester Composition

The epoxidized alkyl ester composition includes a compound of Chemical Formula 2. The epoxidized alkyl ester composition can impart environmental friendliness to the plasticizer composition and can improve plasticization efficiency, light resistance, and heat resistance.

When the epoxidized alkyl ester composition is applied to the plasticizer composition, an iodine value and an oxirane content thereof can be important factors. In particular, in the case of a plasticizer composition included in a food wrapping material in which environmental friendliness is essential, an iodine value and an oxirane content can be critical to plasticizer properties.

The iodine value indicates a content of double bonds present in a molecule, and the content of double bonds can be the content of double bonds remaining after epoxidation such as epoxidation of a vegetable oil or fatty acid alkyl ester.

In addition, the oxirane content can vary depending on the number of epoxy groups contained in a substituent $R_3$.

That is, the iodine value and oxirane content can be indicators of the extent to which epoxidation has proceeded, so they can be related to each other to a certain extent and can be theoretically inversely proportional to each other.

However, since double bonds of a vegetable oil or fatty acid alkyl ester can vary substantially depending on a substance, the two parameters do not necessarily form an exact inverse or trade-off relationship, and a substance having a higher iodine value can simultaneously have a higher oxirane content between two substances. Therefore, it can be preferable that an epoxidized fatty acid alkyl ester-based substance having an iodine value and an oxirane content within ranges to be described below be applied to a plasticizer composition used for an environmentally-friendly food wrapping material.

The epoxidized alkyl ester composition can have an iodine value of less than 3.5 $I_2$ g/100 g (hereinafter, the unit "$I_2$ g/100 g" is omitted), 3.2 or less, or 3.0 or less, with 3.0 or less being preferred. When the above-described condition is satisfied, a plasticizer composition can realize a color appropriate for use as a food wrapping material, and mechanical properties such as tensile strength, an elongation rate, and the like can also be improved.

The epoxidized alkyl ester composition can have an oxirane content (O.C.) of 3.5% or more, 4.0% or more, 4.2% or more, or 4.5% or more, with 4.5% or more being preferred. When the above-described condition is satisfied, compatibility of a plasticizer composition with a resin is improved, and thus migration and processability can be improved, and mechanical properties such as tensile strength, an elongation rate, and the like can also be improved.

The iodine value and oxirane content of the epoxidized alkyl ester composition can be used to predict the quality of a product, and an oxirane index (O.I.) can be utilized as an index thereof. Generally, an oxirane index can be 1.0 or more, 1.5 or more, or 2.0 or more, with 2.0 or more being preferred.

The "oxirane index" refers to a ratio of an oxirane content of the epoxidized fatty acid alkyl ester compound to an iodine value thereof, and can be a ratio of double bonds epoxidized after epoxidation and remaining unreacted double bonds.

The epoxidized alkyl ester composition can include one or more epoxidized fatty acid alkyl esters (eFAAEs), specifically, one or more compounds of Chemical Formula 2.

$R_3$ in Chemical Formula 2 can be a substituent of the formula

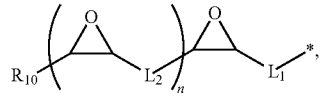

wherein each of $L_1$ and $L_2$ can be a C1 to C10 alkylene group, $R_{10}$ can be a C1 to C19 alkyl group, and n can range from 0 to 5, wherein the sum of the number of carbon atoms in $L_1$, $L_2$, and $R_{10}$ ranges from 8 to 20. Preferably, $L_1$ is a C5 to C10 alkylene group, $L_2$ is a C1 to C3 alkylene group, and $R_{10}$ is a C1 to C10 alkyl group.

$R_4$ in Chemical Formula 2 can be a C4 to C10 alkyl group or a C4 to C9 alkyl group, with a C4 to C9 alkyl group being preferred. When $R_4$ is an alkyl group having less than 4 carbon atoms, migration and volatile loss of a plasticizer composition can be considerably poor, and there can be problems of air pollution caused by volatilization during processing, degradation of tensile strength of a final product, and the like. On the other hand, when $R_4$ is an alkyl group having greater than 10 carbon atoms, the molecular weight is too high, and thus there can be a problem in migration caused by degradation of plasticization efficiency and compatibility with a resin.

$R_4$ can be one or more selected from the group consisting of a butyl group (abbreviated as B), an isobutyl group (abbreviated as iB), a pentyl group (abbreviated as P), an isopentyl group (abbreviated as iP), a hexyl group (abbreviated as Hx), an isohexyl group (abbreviated as iHx), a heptyl group (abbreviated as Hp), an isoheptyl group (abbreviated as iHp), an octyl group (abbreviated as nO), an isooctyl group (abbreviated as iO), a 2-ethylhexyl group (abbreviated as EH or O), a nonyl group (abbreviated as nN), an isononyl group (abbreviated as iN), a 6-methyloctyl group (abbreviated as MO), a decyl group (abbreviated as D), a decyl group (abbreviated as D), an isodecyl group (abbreviated as iD), and a 2-propylheptyl group (abbreviated as PH), with one or more selected from the group consisting of a butyl group, an isobutyl group, a 2-ethylhexyl group, an octyl group, an isononyl group, and a 2-propylheptyl group being preferred.

Here, specific examples of the isopentyl group include a 2-methylbutyl group, and specific examples of the isohexyl group include a 2-methylpentyl group, a 3-methylpentyl group, a 4-methylpentyl group, a 2,2-dimethylbutyl group, a 2,3-dimethylbutyl group, a 2-ethylbutyl group, and the like.

The epoxidized alkyl ester composition can include one or more compounds of the following Chemical Formulas 2-1 to 2-18:

<Chemical Formula 2-1>

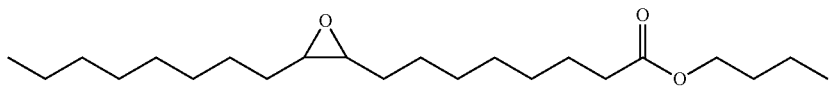

<Chemical Formula 2-2>

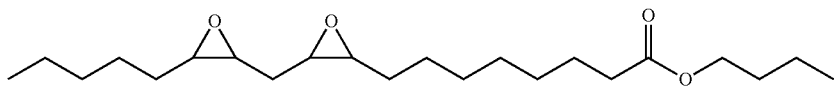

-continued
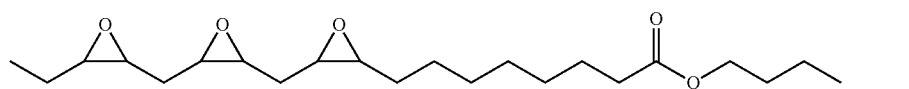
<Chemical Formula 2-3>
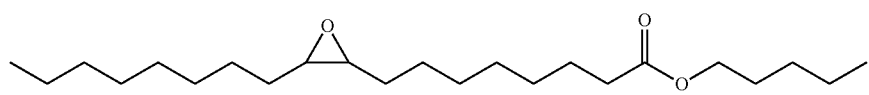
<Chemical Formula 2-4>
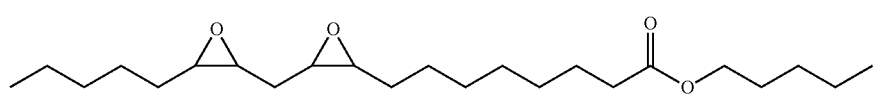
<Chemical Formula 2-5>
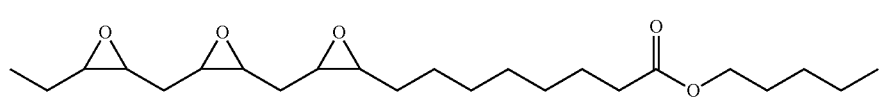
<Chemical Formula 2-6>
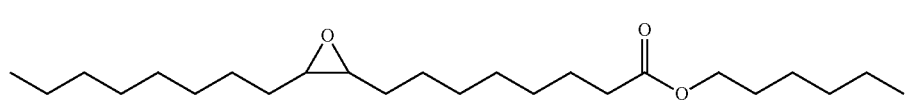
<Chemical Formula 2-7>
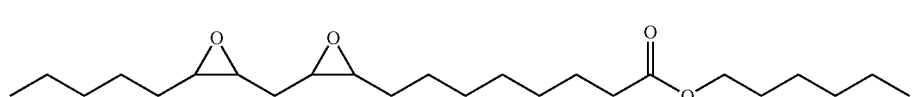
<Chemical Formula 2-8>
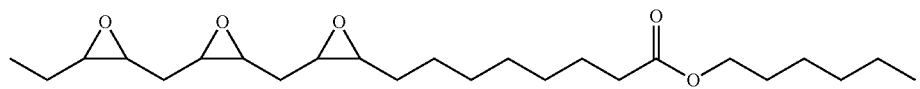
<Chemical Formula 2-9>
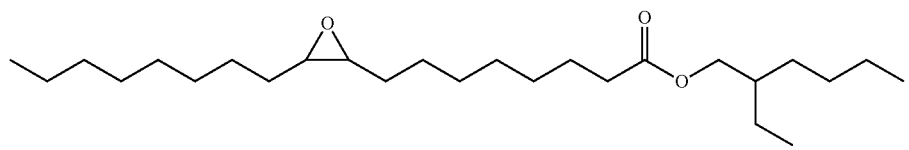
<Chemical Formula 2-10>
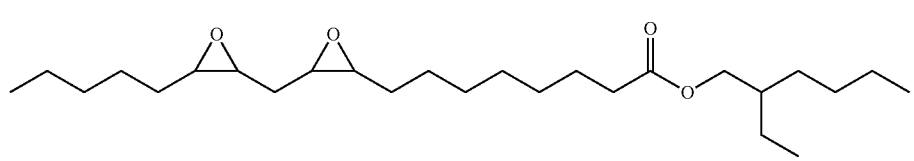
<Chemical Formula 2-11>
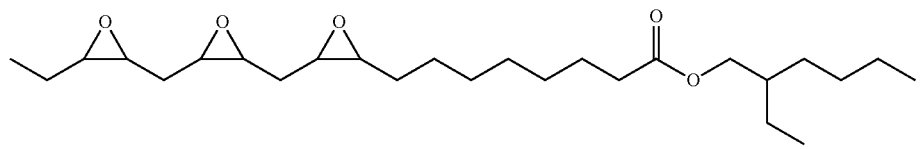
<Chemical Formula 2-12>
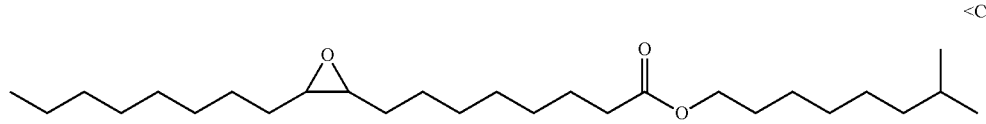
<Chemical Formula 2-13>
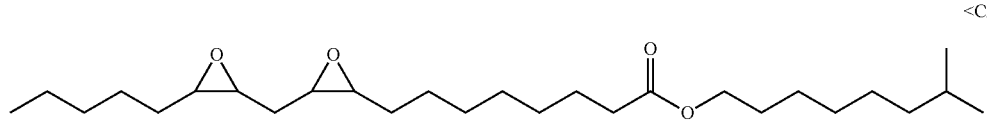
<Chemical Formula 2-14>
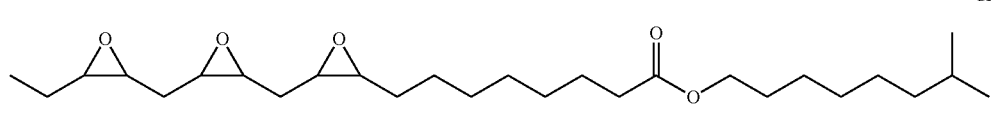
<Chemical Formula 2-15>

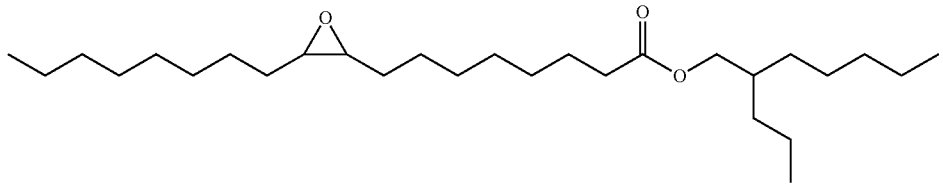
<Chemical Formula 2-16>

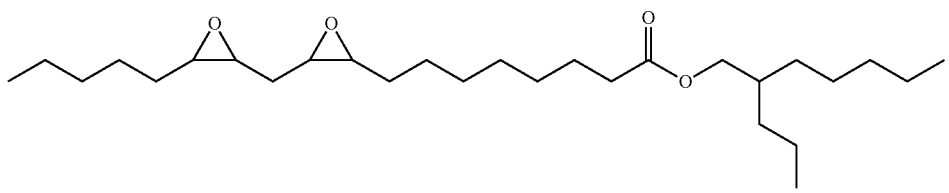
<Chemical Formula 2-17>

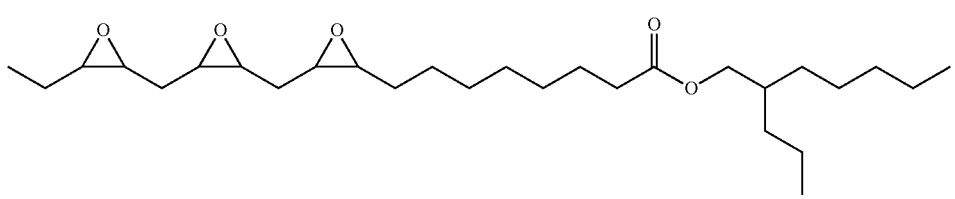
<Chemical Formula 2-18>

The epoxidized alkyl ester composition includes the epoxidized alkyl ester composition including one or more compounds of Chemical Formula 2, and can further include a saturated fatty acid alkyl ester composition including one or more compounds of the following Chemical Formula 4:

Chemical Formula 4

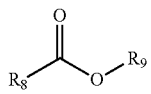

wherein in Chemical Formula 4:
$R_8$ is a C8 to C20 alkyl group; and
$R_9$ is a C4 to C10 alkyl group.

In the saturated fatty acid alkyl ester composition including one or more compounds of Chemical Formula 4, $R_8$ may not include an epoxy group. In a process of preparing an epoxidized fatty acid alkyl ester using an epoxidized oil and an alcohol, a fatty acid moiety of the epoxidized oil can be varied, there can be a fatty acid moiety that is not bound to an epoxy group, and the compound of Chemical Formula 4 can result from such a fatty acid moiety.

However, when a content of the saturated fatty acid alkyl ester composition is about 80 wt % or more with respect to the total secondary plasticizer including the epoxidized alkyl ester composition, compatibility with a vinyl chloride resin can be degraded. Therefore, when a content of the composition is 70 wt % or less, preferably 50 wt % or less, and more preferably 30 wt % or less, excellent compatibility with a vinyl chloride resin can be exhibited.

Here, the secondary plasticizer can refer to the epoxidized alkyl ester composition including one or more compounds of Chemical Formula 2, among components of the plasticizer composition according to the present invention.

The epoxidized alkyl ester composition can further include one or more of compounds of the following Chemical Formulas 4-1 to 4-12:

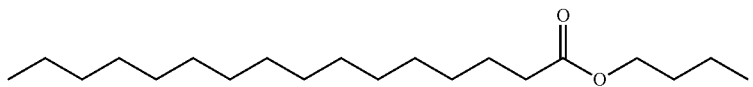
<Chemical Formula 4-1>

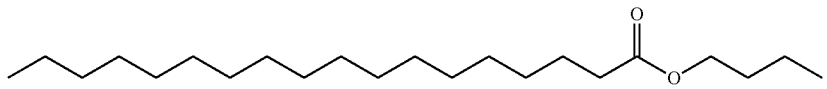
<Chemical Formula 4-2>

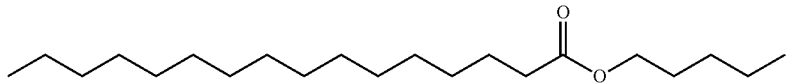
<Chemical Formula 4-3>

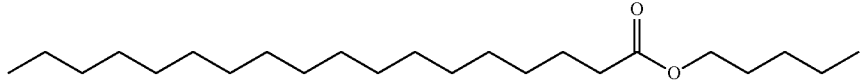
<Chemical Formula 4-4>

<Chemical Formula 4-5>

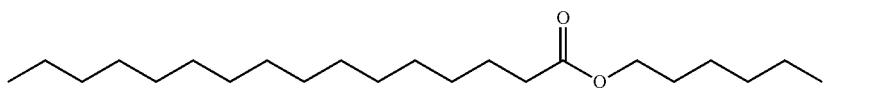

<Chemical Formula 4-6>

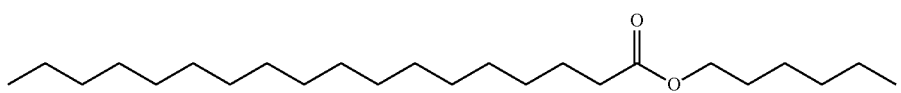

<Chemical Formula 4-7>

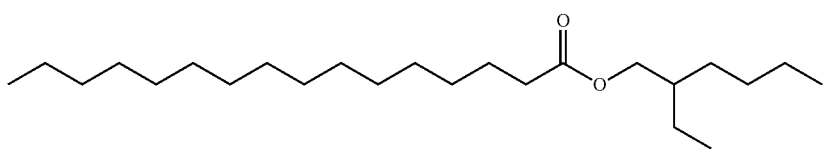

<Chemical Formula 4-8>

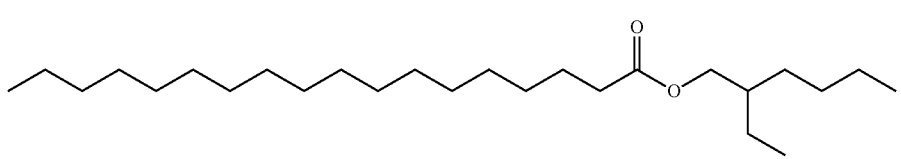

<Chemical Formula 4-9>

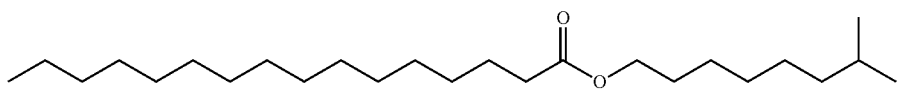

<Chemical Formula 4-10>

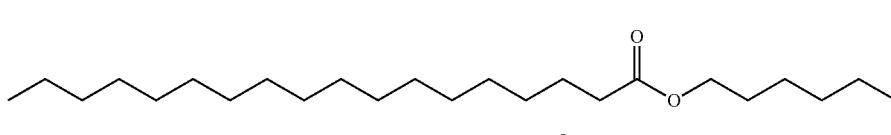

<Chemical Formula 4-11>

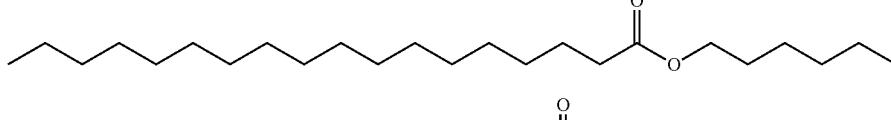

<Chemical Formula 4-12>

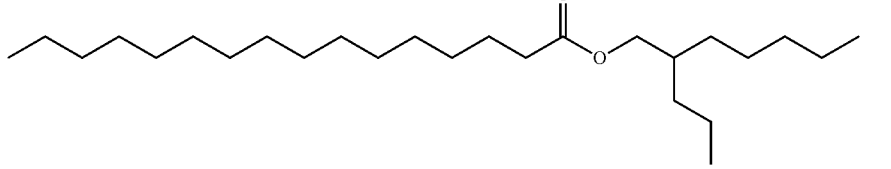

The epoxidized alkyl ester composition can be included in amount of 5 to 70 wt %, 5 to 60 wt %, or 10 to 50 wt % with respect to the total weight of the plasticizer composition, with the range of 10 to 50 wt % being preferred. When the above-described condition is satisfied, plasticization efficiency, volatile loss, and thermal stability can be improved.

The epoxidized alkyl ester composition can be prepared by direct esterification or trans-esterification of an epoxidized oil and a C4 to C10 alcohol.

The epoxidized oil can be a compound prepared by introducing a predetermined amount of epoxy groups through epoxidation of a vegetable oil, that is, one or more selected from the group consisting of epoxidized soybean oil, epoxidized castor oil, epoxidized linseed oil, epoxidized palm oil, an epoxidized stearate, an epoxidized oleate, epoxidized tall oil, and an epoxidized linoleate.

The epoxidized oil can be, for example, one or more of epoxidized oils of the following Chemical Formulas 5 to 11:

Chemical Formula 5

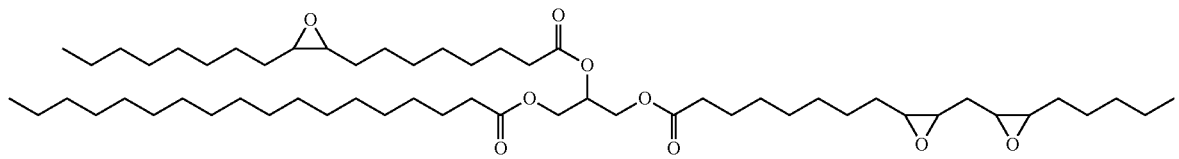

Chemical Formula 6

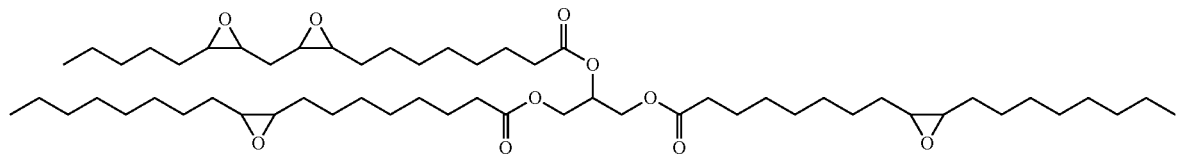

Chemical Formula 7

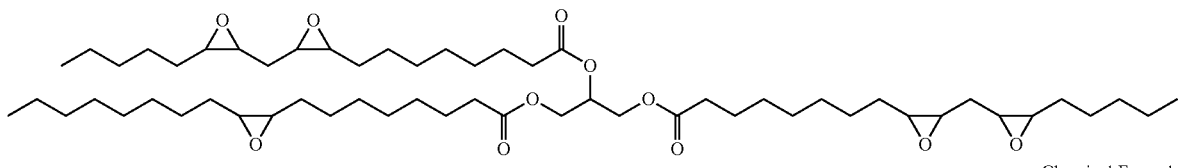

Chemical Formula 8

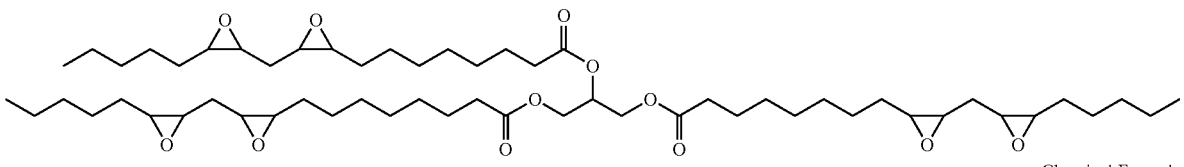

Chemical Formula 9

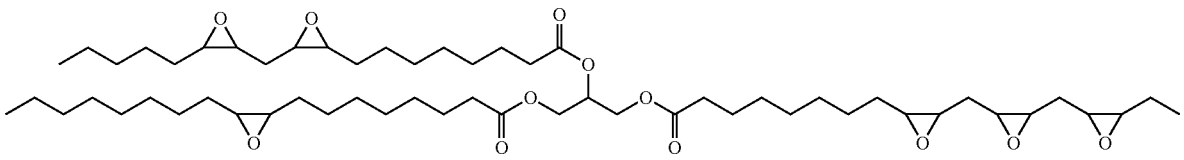

Chemical Formula 10

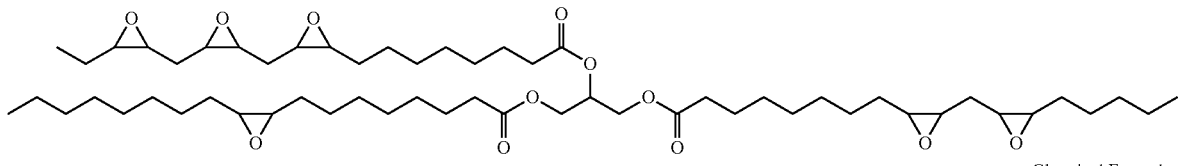

Chemical Formula 11

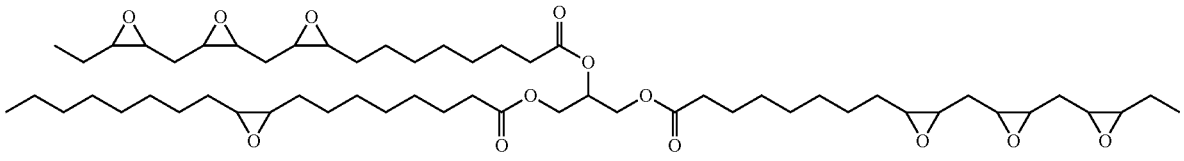

The epoxidized oils of Chemical Formulas 5 to 11 include three ester groups and one or more epoxy groups in one molecule.

When the epoxidized oils of Chemical Formulas 5 to 11 and the C4 to C10 alcohol are trans-esterified, the three ester groups can be separated into three ester compounds, and the separated ester compounds react with the alkyl group of the alcohol, thereby forming an epoxidized alkyl ester composition.

The trans-esterification can be performed at a temperature of 40 to 230° C., 50 to 200° C., or 50 to 180° C. for 10 minutes to 10 hours, 30 minutes to 8 hours, or 1 to 6 hours.

Within the above-described temperature and time ranges, a desired epoxidized alkyl ester-based substance can be effectively obtained. Here, the reaction time can be calculated from the point of time at which the reaction temperature is reached after raising the temperature of the reactants.

The trans-esterification can be performed in the presence of a basic catalyst, acidic catalyst, or metal catalyst, which provides an effect of reducing the reaction time.

Examples of the acidic catalyst include sulfuric acid, methanesulfonic acid, p-toluenesulfonic acid, and the like, and examples of the metal catalyst include an alkoxide-based organometallic catalyst, a metal oxide catalyst, a metal salt catalyst, and a metal itself, which includes sodium, potassium, or the like.

A metal component of the metal catalyst can be, for example, any one or a mixture of two or more metals selected from the group consisting of sodium, potassium, tin, titanium, and zirconium.

In addition, a process of removing, after the trans-esterification, a produced polyhydric alcohol and reaction by-products and an unreacted alcohol through separation, washing, and distillation can be further performed.

In the purification process, specifically, cooling and maintaining the products, the unreacted alcohol, and the like at 80 to 100° C. for a predetermined time can be performed after the trans-esterification. In this case, layer separation occurs, and this can result in an upper layer containing an epoxidized alkyl ester and an alcohol and a lower layer containing glycerine and other by-products. Next, in order to neutralize a catalyst, an aqueous solution for neutralizing a catalyst can be added to induce neutralization and washing.

The neutralization and washing processes can be performed after a lower layer containing most of the by-products is first separated. In the neutralization and washing processes, the by-products included in the lower layer can be dissolved in water and discharged. Afterward, washing can be repeatedly performed to recover and remove an unreacted alcohol and moisture.

However, it can be necessary to vary the neutralization and washing processes according to the number of carbon atoms of an alcohol used in the trans-esterification.

For example, in the case of using butanol having 4 carbon atoms, when the neutralization and washing processes are directly performed, waste water can be produced, and therefore, it can be preferable to remove butanol through distillation in advance. However, in this case, since the catalyst remains active, glycerol as a by-product and an epoxidized alkyl ester as a product can be reversely reacted to produce an epoxidized oil-like substance such as a diglyceride, a triglyceride, or the like. Therefore, it is necessary to design the process with caution.

As another example, in the case of using 2-ethylhexyl alcohol having 8 carbon atoms, waste water is not produced due to low solubility of 2-ethylhexyl alcohol in water. Therefore, both cases in which an alcohol is removed after neutralization and washing processes and in which neutralization and washing processes are performed after by-products in a lower layer are removed can proceed without critical problems.

3) Citrate-Based Substance

The citrate-based substance has a structure of Chemical Formula 3 and can improve an absorption rate, plasticization efficiency, migration resistance, and the like of the plasticizer composition.

When a citrate-based substance including an acetyl group instead of a hydroxyl group in Chemical Formula 3 is used, physical properties (e.g., plasticization efficiency) of a plasticizer composition can be degraded. In addition, processes, time, and facility costs for disposal of waste acetic acid generated as a by-product during the preparation of a citrate-based substance can be additionally required, which leads to an increase in manufacturing costs.

Accordingly, a citrate-based substance including an acetyl group instead of a hydroxyl group in Chemical Formula 3 exhibits degraded plasticization efficiency compared to the citrate-based substance of Chemical Formula 3, and an additional amount of the citrate-based substance needs to be increased to overcome the degraded plasticization efficiency, and thus the price of a product can be increased. Therefore, considering various aspects such as marketability, economic feasibility, physical properties, and the like, a citrate-based substance including an acetyl group is not preferred.

$R_5$ to $R_7$ in Chemical Formula 3 each independently are a C4 to C10 alkyl group, preferably, a C4 to C8 alkyl group or a C5 to C10 alkyl group.

When the above-described condition is satisfied, the citrate-based substance has an appropriate molecular weight, and thus plasticization efficiency and an absorption rate of the plasticizer composition can be improved.

When $R_5$ to $R_7$ each independently are alkyl groups having less than 4 carbon atoms, tensile strength and volatile loss of the plasticizer composition are degraded, thereby resulting in degradation of quality of a final product and a relative increase in an amount of the composition volatilized during processing, which increases the possibility of adverse effects on the atmosphere. In addition, to overcome these problems, excess plasticizer composition needs to be added in an amount as much as the volatilized amount, and thus it is economically disadvantageous.

When $R_5$ to $R_7$ each independently are alkyl groups having greater than 10 carbon atoms, the molecular weight of the citrate-based substance is increased, and thus plasticization efficiency and an absorption rate of the plasticizer composition are rather degraded.

Meanwhile, in the calendering industry that requires, as key quality factors, plasticization efficiency, an absorption rate, and migration, $R_5$ to $R_7$ are preferably a C4 to C8 alkyl group, more preferably a C4 to C6 alkyl group. In addition, in the compound industry that requires, as key quality factors, tensile strength and tensile retention, an elongation rate and elongation retention, volatile loss, and the like, $R_5$ to $R_7$ are preferably a C5 to C10 alkyl group, more preferably a C8 to C10 alkyl group.

$R_5$ to $R_7$ each independently are one or more selected from the group consisting of an n-butyl group, an isobutyl group, an n-pentyl group, an isopentyl group, an n-hexyl group, an isohexyl group, an n-heptyl group, an isoheptyl group, an n-octyl group, an isooctyl group, a 2-ethylhexyl group, an n-nonyl group, an isononyl group, a 2-propylheptyl group, and an isodecyl group, with one or more selected from the group consisting of an n-butyl group, an isobutyl group, an n-pentyl group, an isopentyl group a 2-ethylhexyl group, and an isononyl group being preferred.

Two of $R_5$ to $R_7$ can be the same, and the remaining one can be different. In this case, the citrate-based substance of Chemical Formula 3 can be a citrate group having combined substituents selected from among an n-butyl group, an isobutyl group, an n-pentyl group, an isopentyl group, a 2-ethylhexyl group, and an isononyl group.

Alternatively, $R_5$ to $R_7$ can be the same. In this case, the citrate-based substance of Chemical Formula 3 can be one or more selected from the group consisting of tri-n-butyl citrate (TnBC), triisobutyl citrate (TiBC), tri-n-pentyl citrate (TnPC), triisopentyl citrate (TIPC), trihexyl citrate (THxC), triheptyl citrate (THpC), triisoheptyl citrate (TIHpC), tri(2-ethylhexyl) citrate (TEHC), triisononyl citrate (TINC), and triisodecyl citrate (TIDC).

The citrate-based substance can be included in an amount of 5 to 70 wt %, 5 to 60 wt %, or 10 to 50 wt % with respect to the total weight of the plasticizer composition, with the range of 10 to 50 wt % being preferred.

When the above-described condition is satisfied, quality such as plasticization efficiency, an absorption rate, migration resistance, and the like can be improved.

When the citrate-based substance of Chemical Formula 3 is directly prepared, direct esterification or trans-esterification of citric acid or a derivative thereof with an alcohol can be performed.

The derivative of citric acid can be one or more selected from the group consisting of an anhydride of citric acid and an alkyl ester of citric acid. The alkyl ester can be a C1 to C6 alkyl ester.

The alcohol can be a C4 to C10 alcohol, preferably, a C4 to C8 alcohol or a C5 to C10 alcohol.

When the citrate-based substance of Chemical Formula 3 is prepared by direct esterification or trans-esterification, the alcohol can be used in an amount of 3 to 15 moles, 3 to 12 moles, or 3 to 10 moles with respect to 1 mole of the citric acid or the derivative thereof, with the range of 3 to 10 moles being preferred.

Additional descriptions of direct esterification and transesterification are the same as the descriptions in the preparation method of the cyclohexane-1,4-diester-based substance of Chemical Formula 1.

Meanwhile, the sum of the number of carbon atoms of the alkyl group of $R_4$ and the average number of carbon atoms of the alkyl groups of $R_5$ to $R_7$ can range from 10 to 15. When the above-described range is satisfied, excellent plasticization efficiency is exhibited, and migration loss, volatile loss, tensile strength, an absorption rate, and heat resistance can also be improved. However, below the above-described range, migration loss, tensile strength, and an elongation rate can be significantly degraded. In addition, above the above-described range, migration loss, tensile strength, an elongation rate, and an absorption rate can be significantly degraded.

2. Resin Composition

A resin composition according to another embodiment of the present invention includes: a resin in an amount of 100 parts by weight; and the plasticizer composition according to an embodiment of the present invention in an amount of 5 to 150 parts by weight.

The resin can be any resin known in the art. For example, a mixture of one or more selected from the group consisting of a straight vinyl chloride polymer, a paste vinyl chloride polymer, an ethylene-vinyl acetate copolymer, an ethylene polymer, a propylene polymer, polyketone, polystyrene, polyurethane, natural rubber, synthetic rubber, and a thermoplastic elastomer can be used, but the present invention is not limited thereto.

The plasticizer composition can be included in an amount of 5 to 150 parts by weight, preferably, 5 to 130 parts by weight, or 10 to 120 parts by weight with respect to 100 parts by weight of the resin.

In general, a resin in which a plasticizer composition is used can be subjected to melt processing or plastisol processing to prepare a resin product, and the resin for melt processing and the resin for plastisol processing can be produced differently according to a polymerization method.

For example, when used in melt processing, a vinyl chloride polymer is prepared through suspension polymerization or the like and thus used as a solid-phase resin particle having a large average particle diameter. In this case, the vinyl chloride polymer is called a straight vinyl chloride polymer. When used in plastisol processing, a vinyl chloride polymer is prepared through emulsion polymerization or the like and thus used as a fine sol-phase resin particles. In this case, the vinyl chloride polymer is called a paste vinyl chloride polymer.

In the case of the straight vinyl chloride polymer, the plasticizer composition is preferably included in an amount of 5 to 80 parts by weight with respect to 100 parts by weight of the polymer, and in the case of the paste vinyl chloride polymer, the plasticizer composition is preferably included in an amount of 40 to 120 parts by weight with respect to 100 parts by weight of the polymer.

The resin composition can further include a filler. The filler can be included in an amount of 0 to 300 parts by weight, preferably 50 to 200 parts by weight, and more preferably 100 to 200 parts by weight with respect to 100 parts by weight of the resin.

The filler can be any filler known in the art without particular limitation. For example, a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate, and barium sulfate can be used.

In addition, the resin composition can further include other additives such as a stabilizer and the like as necessary. The additives such as a stabilizer and the like can be included, for example, in an amount of 0 to 20 parts by weight, preferably 1 to 15 parts by weight with respect to 100 parts by weight of the resin.

Examples of the stabilizer include a calcium-zinc (Ca—Zn)-based stabilizer such as a complex stearate of calcium and zinc and the like and a barium-zinc (Ba—Zn)-based stabilizer, but the present invention is not particularly limited thereto.

The resin composition can be applied to both melt processing and plastisol processing as described above, wherein the melt processing can be, for example, calendering processing, extrusion processing, or injection processing, and the plastisol processing can be coating processing or the like.

Hereinafter, the present invention will be described in detail with reference to embodiments so that those skilled in the art can easily carry out the present invention. However, the present invention can be embodied in several different forms, and therefore, is not limited to embodiments described herein.

Preparation Example 1

516.5 g of cyclohexane-1,4-dicarboxylic acid, 1,170 g of 2-ethylhexanol, and 1.55 g of tetraisopropyl titanate as a catalyst were put into a 3 L four-neck reaction vessel equipped with a cooler, a condenser, a decanter, a reflux pump, a temperature controller, a stirrer, and the like, and then the temperature of the reaction vessel was set at 230° C. Then, esterification was performed for 6 hours while continuously introducing nitrogen gas and terminated when an acid value reached 0.1.

After the reaction was completed, distillation extraction was performed under reduced pressure to remove unreacted raw materials. Afterward, neutralization, dehydration, and filtration processes were performed to prepare 1,154 g of di(2-ethylhexyl) cyclohexane-1,4-dicarboxylate (1,4-DEHCH) (yield: 97%).

Preparation Example 2: Preparation of eFABE 1,000 g of epoxidized soybean oil (ESO) having an oxirane content of 6.97% and an iodine value of 1.93 (12 g/100 g), 500 g of butanol, and 5.5 g of tetra(n-butyl) titanate as a catalyst were put into a 3 L four-neck reaction vessel equipped with a cooler, a condenser, a decanter, a reflux pump, a temperature controller, a stirrer, and the like, and the temperature of the reaction vessel was gradually raised up to about 180° C.

After it was confirmed that the raw material ESO was completely reacted and consumed through gas chromatography analysis, the reaction was terminated. Afterward, glycerine as a by-product and unreacted raw materials were removed, and a product was purified, thereby finally obtaining 1,160 g of an epoxidized fatty acid butyl ester composition (eFABE) having an oxirane content of 5.18% and an iodine value of 1.68 and including compounds of the following Chemical Formulas 2-1, 2-2, 2-3, 4-1, and 4-2.

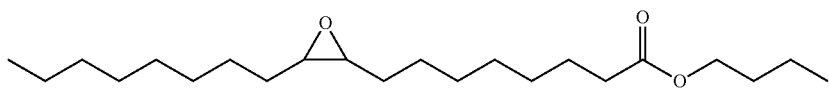

<Chemical Formula 2-1>

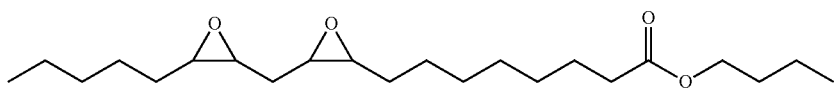

<Chemical Formula 2-2>

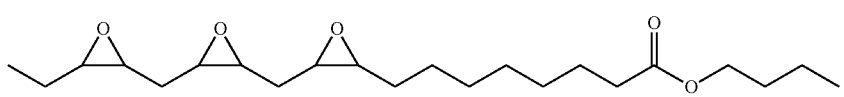

<Chemical Formula 2-3>

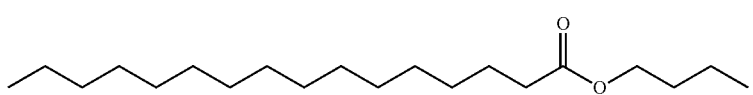

<Chemical Formula 4-1>

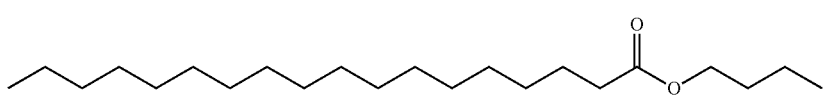

<Chemical Formula 4-2>

Preparation Example 3: Preparation of eFAPE 1,180 g of an epoxidized fatty acid pentyl ester composition (eFAPE) was prepared in the same manner as in Preparation Example 2 except that 500 g of 1-pentanol was used instead of butanol. In this case, the eFAPE had an oxirane content of 5.51% and an iodine value of 1.40 and included compounds of the following Chemical Formulas 2-4, 2-5, 2-6, 4-3, and 4-4.

Preparation Example 4: Preparation of eFAHxE 1,180 g of an epoxidized fatty acid hexyl ester composition (eFAHxE) was prepared in the same manner as in Preparation Example 2 except that 500 g of 1-hexanol was used instead of butanol. In this case, an epoxidized fatty acid pentyl ester composition had an oxirane content of 5.51% and an iodine value of 1.40 and included compounds of the following Chemical Formulas 2-7, 2-8, 2-9, 4-5, and 4-6.

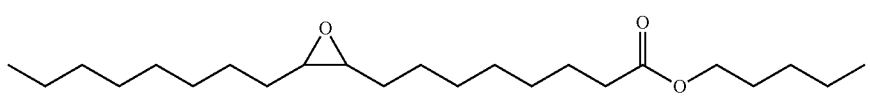

<Chemical Formula 2-4>

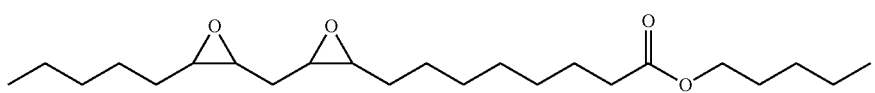

<Chemical Formula 2-5>

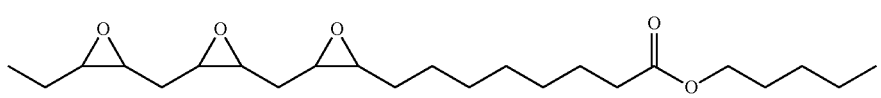

<Chemical Formula 2-6>

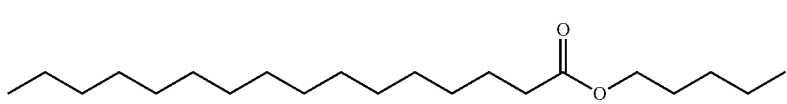

<Chemical Formula 4-3>

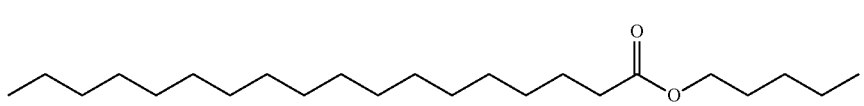

<Chemical Formula 4-4>

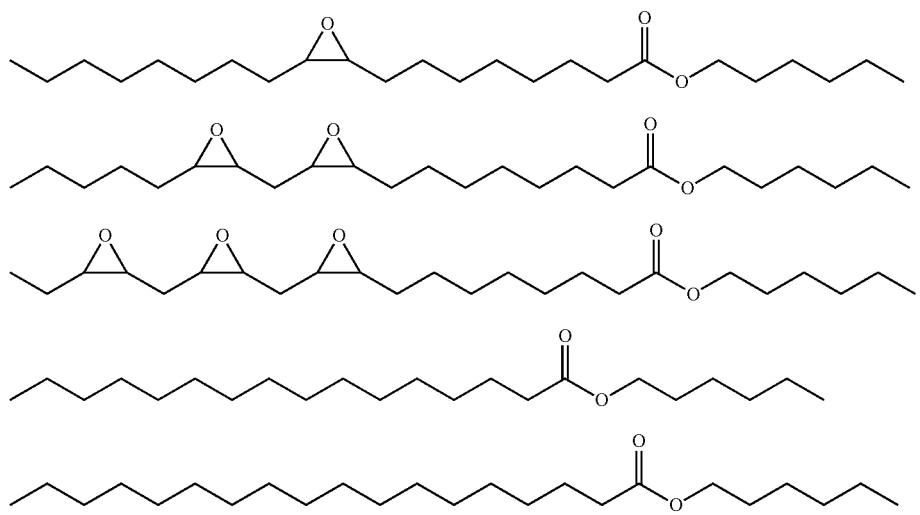

<Chemical Formula 2-7>

<Chemical Formula 2-8>

<Chemical Formula 2-9>

<Chemical Formula 4-5>

<Chemical Formula 4-6>

Preparation Example 5: Preparation of eFAEHE 1,180 g of an epoxidized fatty acid ethylhexyl ester composition (eFAEHE) having an oxirane content of 5.21% and an iodine value of 1.70 and including compounds of the following Chemical Formulas 2-10, 2-11, 2-12, 4-7, and 4-8 was obtained in the same manner as in Preparation Example 2 except that 500 g of 2-ethylhexanol was used instead of butanol.

Preparation Example 6: Preparation of eFAINE 1,250 g of an epoxidized fatty acid isononyl ester composition (eFAINE) having an oxirane content of 5.22% and an iodine value of 1.72 and including compounds of the following Chemical Formulas 2-13, 2-14, 2-15, 4-9, and 4-10 was obtained in the same manner as in Preparation Example 2 except that 600 g of isononanol was used instead of butanol.

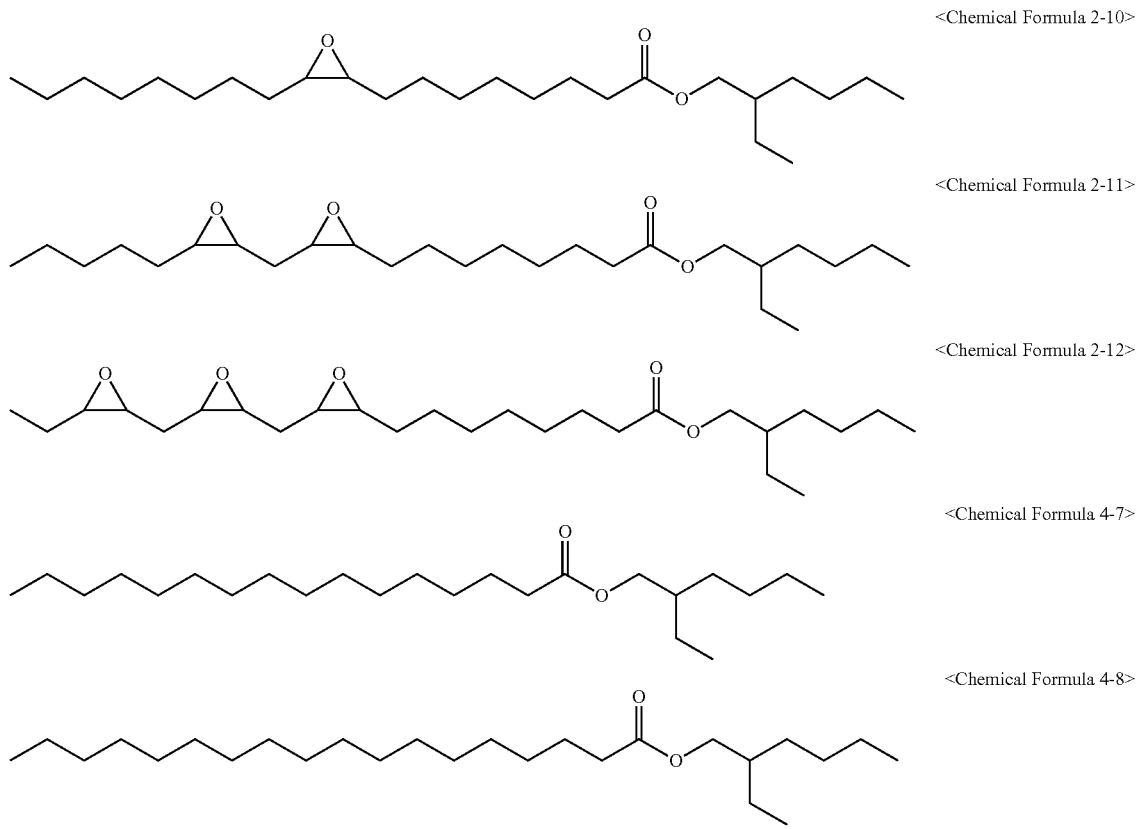

<Chemical Formula 2-10>

<Chemical Formula 2-11>

<Chemical Formula 2-12>

<Chemical Formula 4-7>

<Chemical Formula 4-8>

<Chemical Formula 2-13>

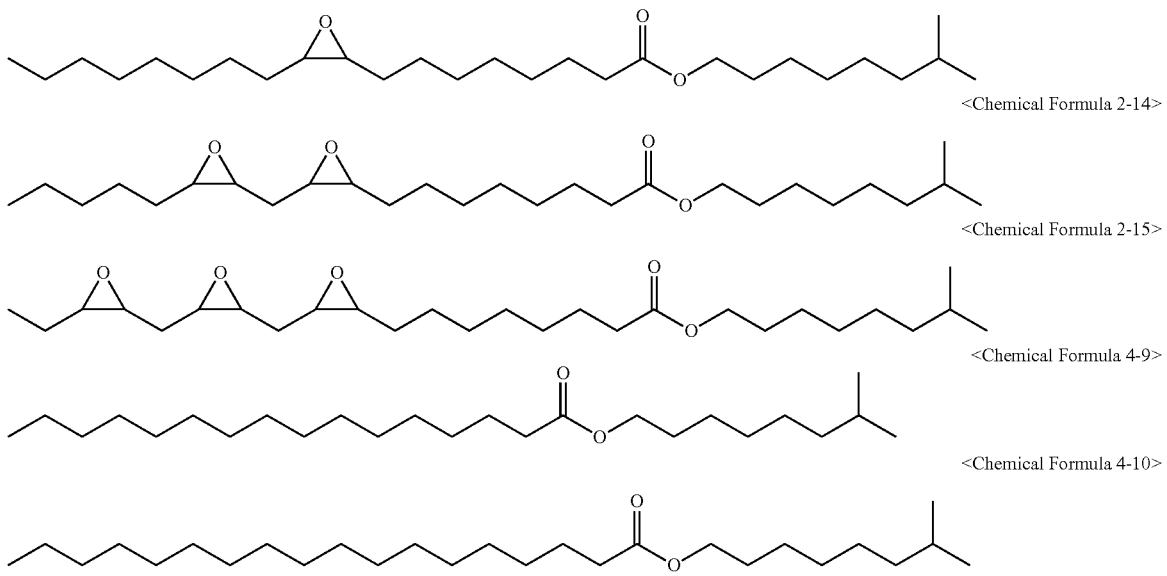

<Chemical Formula 2-14>

<Chemical Formula 2-15>

<Chemical Formula 4-9>

<Chemical Formula 4-10>

Preparation Example 7: Preparation of eFAPHE 1,280 g of an epoxidized fatty acid propylheptyl ester composition (eFAPHE) having an oxirane content of 5.00% and an iodine value of 1.47 and including compounds of the following Chemical Formulas 2-16, 2-17, 2-18, 4-11, and 4-12 was obtained in the same manner as in Preparation Example 2 except that 600 g of 2-propylheptanol was used instead of butanol.

<Chemical Formula 2-16>

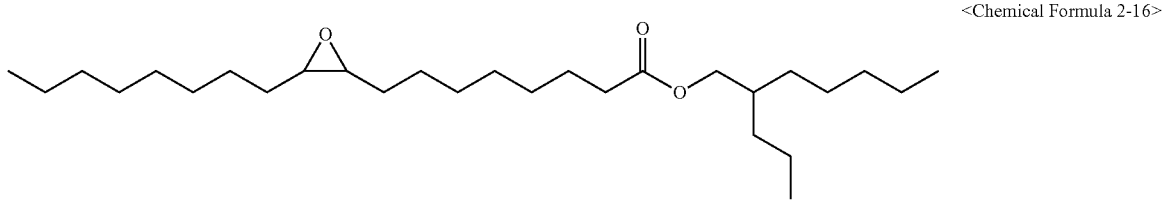

<Chemical Formula 2-17>

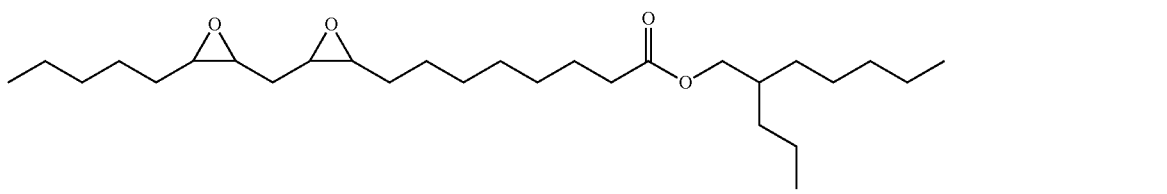

<Chemical Formula 2-18>

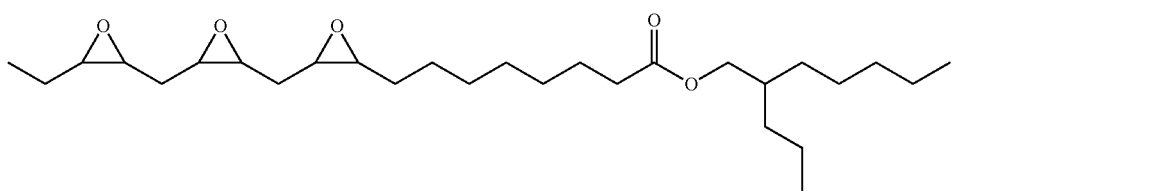

<Chemical Formula 4-11>

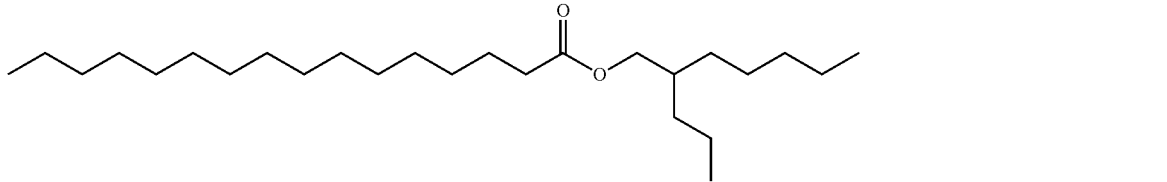

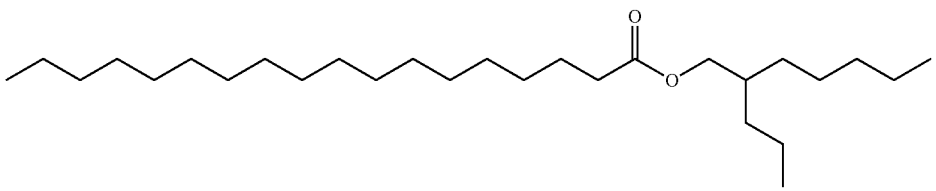

<Chemical Formula 4-12>

The substances according to Preparation Examples were mixed in contents as described in Table 1 to Table 5 below and stirred, thereby preparing plasticizer compositions. Physical properties of the plasticizer compositions were evaluated according to the following test items.

<Test Items>

Measurement of hardness (Shore "A" and Shore "D")

In accordance with ASTM D2240, the hardness of a 3 mm-thick specimen was measured for 10 seconds.

Measurement of Migration Loss (%)

In accordance with KSM-3156, glass plates were attached to both sides of a 1 mm-thick specimen, and a load of 1 kgf/cm² was then applied thereto. The specimen was placed in a hot-air convection oven (80° C.) for 72 hours, then taken out of the oven, and cooled at room temperature. Afterward, the glass plates attached to both sides of the specimen were removed, weights of the specimen before being placed in and after taken out of the oven were measured, and the resultant weights were substituted into the following Equation 1 to obtain a migration loss value:

Migration loss (%)=[(Initial weight of specimen before being placed in oven)−(Weight of specimen after taken out of oven)]/(Initial weight of specimen before being placed in oven)×100  <Equation 1>

Measurement of Volatile Loss (%)

A 1 mm-thick specimen was exposed to 80° C. for 72 hours, a weight thereof was then measured, and the resultant weight was substituted into the following Equation 2 to obtain a volatile loss value:

Volatile loss (%)=[(Initial weight of specimen)−(Weight of specimen after being exposed)]/(Initial weight of specimen)×100  <Equation 2>

Measurement of Tensile Strength (kgf/cm²)

In accordance with ASTM D638, a 1 mm-thick specimen was pulled at a cross head speed of 200 mm/min using a universal testing machine (UTM; 4466 manufactured by Instron), and a time point at which the specimen was broken was then determined.

Measurement of Elongation Rate (%)

In accordance with ASTM D638, a 1 mm-thick specimen was pulled at a cross head speed of 200 mm/min using a universal testing machine (UTM; 4466 manufactured by Instron), and a time point at which the specimen was broken was then determined. Afterward, a length at the time point was substituted into the following Equation 3 to calculate an elongation rate:

Elongation rate (%)=[(Length at the time point when specimen was broken)/(Initial length)]×100  <Equation 3>

Absorption Rate

An absorption rate was evaluated by measuring the time taken to stabilize the torque of a mixer in which a resin and a composition are mixed together using a planetary mixer (Brabender, P600) at 77° C. and 60 rpm.

Heat Resistance

Heat resistance was observed by operating a 0.5 T-thick specimen at a speed of 25 mm/3 min using a Mathis oven at 220° C. and evaluated using 5 scales (1 (excellent) to 5 (poor)).

Experimental Example: Evaluation of Physical Properties

Specimens were prepared using plasticizer compositions of the Examples and Comparative Examples described in Table 1 to Table 5 below.

For specimen preparation, in accordance with ASTM D638, 100 parts by weight of polyvinyl chloride (LS100 manufactured by LG Chem Ltd.), 40 parts by weight of each of the plasticizer compositions prepared in Examples and Comparative Examples, and 3 parts by weight of a stabilizer (BZ153T manufactured by SONGWON) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

The specimens were subjected to tests for evaluating the above-described physical properties, and results thereof are shown in Table 1 to Table 5 below.

TABLE 1

| | Classification | | Examples | | | | |
|---|---|---|---|---|---|---|---|
| | | | 1 | 2 | 3 | 4 | 5 |
| Plasticizer composition (wt %) | Cyclohexane-1,4-diester-based substance | 1,4-DEHCH | 70 | 70 | 70 | 70 | 70 |
| | Epoxidized alkyl ester composition | eFAPE | 10 | — | — | — | — |
| | | eFAEHE | — | 10 | — | — | — |
| | | eFAINE | — | — | 10 | — | — |
| | | eFAPHE | — | — | — | 10 | 10 |
| | Citrate-based substance | TBC | 20 | 20 | 20 | 20 | — |
| | | TPC | — | — | — | — | 20 |
| | Sum of number of carbon atoms of R₄ and average number of carbon atoms of R₅, R₆, and R₇ | | 9 | 12 | 13 | 14 | 15 |

TABLE 1-continued

|  | Classification | | Examples | | | | |
|---|---|---|---|---|---|---|---|
|  | | | 1 | 2 | 3 | 4 | 5 |
| Hardness | | A | 87.2 | 89.2 | 89.6 | 89.7 | 88.0 |
| | | D | 41.5 | 43.2 | 43.0 | 43.1 | 42.0 |
| Migration loss | | | 3.66 | 3.21 | 3.11 | 3.20 | 2.53 |
| Volatile loss | | | 1.94 | 1.54 | 1.35 | 1.20 | 1.42 |
| Tensile strength | | | 208.1 | 230.1 | 235.2 | 238.6 | 235.0 |
| Elongation rate | | | 305.6 | 315.0 | 313.9 | 314.8 | 317.8 |
| Absorption rate | | | 205 | 235 | 250 | 256 | 235 |
| Heat resistance | | | 1 | 1 | 1 | 1 | 1 |

TABLE 2

|  | Classification | | Examples | | | | |
|---|---|---|---|---|---|---|---|
|  | | | 6 | 7 | 8 | 9 | 10 |
| Plasticizer composition (wt %) | Cyclohexane-1,4-diester-based substance | 1,4-DEHCH | 70 | 70 | 70 | 70 | 70 |
| | Epoxidized alkyl ester composition | eFABE | 10 | 10 | — | — | — |
| | | eFAPE | — | — | 10 | 10 | — |
| | | pFAHxE | — | — | — | — | 10 |
| | Citrate-based substance | THxC | 20 | — | 20 | — | — |
| | | TEHC | — | 20 | — | 20 | — |
| | | TPHC | — | — | — | — | 20 |
| | Sum of number of carbon atoms of $R_4$ and average number of carbon atoms of $R_5$, $R_6$, and $R_7$ | | 10 | 12 | 11 | 12 | 16 |
| Hardness | | A | 88.3 | 90.4 | 88.5 | 90.5 | 92.5 |
| | | D | 42.2 | 44.6 | 42.3 | 44.6 | 46.2 |
| Migration loss | | | 2.74 | 3.45 | 2.70 | 3.42 | 4.25 |
| Volatile loss | | | 1.27 | 1.20 | 1.20 | 1.05 | 1.12 |
| Tensile strength | | | 234.5 | 237.8 | 230.9 | 235.0 | 204.6 |
| Elongation rate | | | 325.0 | 319.5 | 324.1 | 320.5 | 287.5 |
| Absorption rate | | | 254 | 291 | 262 | 298 | 310 |
| Heat resistance | | | 1 | 1 | 1 | 1 | 1 |

TABLE 3

|  | Classification | | Examples | | | | |
|---|---|---|---|---|---|---|---|
|  | | | 11 | 12 | 13 | 14 | 15 |
| Plasticizer composition (wt %) | Cyclohexane-1,4-diester-based substance | 1,4-DEHCH | 90 | 80 | 60 | 50 | 30 |
| | Epoxidized alkyl ester composition | eFABE | — | — | — | — | 30 |
| | | eFAEHE | 5 | 10 | 20 | 20 | — |
| | Citrate-based substance | TBC | 5 | 10 | 20 | 30 | — |
| | | TINC | — | — | — | — | 40 |
| | Sum of number of carbon atoms of $R_4$ and average number of carbon atoms of $R_5$, $R_6$, and $R_7$ | | 12 | 12 | 12 | 12 | 13 |
| Hardness | | A | 90.1 | 89.9 | 89.3 | 88.6 | 89.4 |
| | | D | 43.7 | 44.0 | 43.3 | 43.0 | 43.3 |
| Migration loss | | | 3.46 | 3.56 | 3.20 | 2.53 | 2.68 |
| Volatile loss | | | 1.27 | 1.40 | 1.34 | 1.60 | 1.06 |
| Tensile strength | | | 230.8 | 235.1 | 230.5 | 235.9 | 238.6 |
| Elongation rate | | | 304.7 | 306.6 | 306.9 | 315.0 | 314.3 |
| Absorption rate | | | 285 | 274 | 248 | 217 | 295 |
| Heat resistance | | | 1 | 1 | 1 | 1 | 1 |

TABLE 4

| Classification | | | Comparative Examples | | | | |
| --- | --- | --- | --- | --- | --- | --- | --- |
| | | | 1 | 2 | 3 | 4 | 5 |
| Plasticizer composition (wt %) | Cyclohexane-1,4-diester-based substance | 1,4-DBCH | — | — | — | 80 | — |
| | | 1,4-DEHCH | 100 | 80 | 80 | — | — |
| | | 1,4-DIDCH | — | — | — | — | 80 |
| | Epoxidized alkyl ester composition | eFABE | — | 20 | — | — | — |
| | | eFAEHE | — | — | — | 10 | 10 |
| | Citrate-based substance | TBC | — | — | 20 | 10 | 10 |
| | Sum of number of carbon atoms of $R_4$ and average number of carbon atoms of $R_5$, $R_6$, and $R_7$ | | — | 4 | 4 | 14 | 14 |
| Hardness | | A | 90.5 | 89.7 | 89.4 | 86.4 | 92.8 |
| | | D | 44.8 | 43.7 | 4.7 | 41.6 | 46.2 |
| Migration loss | | | 4.15 | 3.85 | 3.68 | 6.02 | 2.76 |
| Volatile loss | | | 1.68 | 1.80 | 1.75 | 5.48 | 0.69 |
| Tensile strength | | | 216.3 | 218.4 | 216.0 | 195.6 | 228.6 |
| Elongation rate | | | 295.0 | 300.5 | 295.6 | 270.6 | 286.7 |
| Absorption rate | | | 307 | 280 | 234 | 190 | 318 |
| Heat resistance | | | 3 | 1 | 5 | 1 | 1 |

TABLE 5

| Classification | | | Comparative Examples | | | |
| --- | --- | --- | --- | --- | --- | --- |
| | | | 6 | 7 | 8 | 9 |
| Plasticizer composition (wt %) | Cyclohexane-1,4-diester-based substance | 1,4-DBCH | — | 70 | — | — |
| | | 1,4-DEHCH | — | — | — | 60 |
| | | 1,4-DIDCH | — | — | 70 | — |
| | Epoxidized alkyl ester composition | eFABE | 50 | — | — | — |
| | | eFAEHE | — | 30 | 30 | 20 |
| | Citrate-based substance | TBC | 50 | — | — | — |
| | | ATBC | — | — | — | 20 |
| | Sum of number of carbon atoms of $R_4$ and average number of carbon atoms of $R_5$, $R_6$, and $R_7$ | | 8 | 8 | 8 | — |
| Hardness | | A | 84.5 | 86.1 | 93.4 | 90.4 |
| | | D | 40.1 | 41.5 | 46.8 | 44.6 |
| Migration loss | | | 8.44 | 6.34 | 3.40 | 3.24 |
| Volatile loss | | | 12.03 | 5.88 | 0.67 | 1.33 |
| Tensile strength | | | 180.3 | 187.6 | 230.4 | 221.0 |
| Elongation rate | | | 248.9 | 265.1 | 274.8 | 301.5 |
| Absorption rate | | | 157 | 184 | 357 | 270 |
| Heat resistance | | | 3 | 1 | 1 | 2 |

1,4-DBCH: Dibutyl cyclohexane-1,4-dicarboxylate (LG Chem Ltd.)

1,4-DIDCH: Diisodecyl cyclohexane-1,4-dicarboxylate (LG Chem Ltd.)

TBC: Tributyl citrate (LG Chem Ltd.)
TPC: Tripentyl citrate (LG Chem Ltd.)
THxC: Trihexyl citrate (LG Chem Ltd.)
TEHC: Tris(2-ethylhexyl) citrate (LG Chem Ltd.)
TINC: Triisononyl citrate (LG Chem Ltd.)
TPHC: Tris(2-propylheptyl) citrate (LG Chem Ltd.)
ATBC: Acetyl tributyl citrate (LG Chem Ltd.)

Referring to Table 1 to Table 5, it can be seen that Example 1 to Example 15 are excellent in all of plasticization efficiency, migration loss, volatile loss, tensile strength, an elongation rate, an absorption rate, and heat resistance. In addition, referring to Examples 1 to 10, it can be seen that Examples 2 to 9, in which the sum of the number of carbon atoms of $R_4$ and the average number of carbon atoms of $R_5$, $R_6$, and $R_7$ ranges from 10 to 15, are significantly excellent in migration loss, volatile loss, tensile strength, and an elongation rate compared to Example 1 and Example 10. Additionally, referring to Examples 1 to 4, it can be seen that as the number of carbon atoms of $R_4$ of the epoxidized alkyl ester composition increases, migration loss, volatile loss, tensile strength, and an elongation rate are improved. In addition, referring to Examples 6 to 9, it can be seen that as the average number of carbon atoms of $R_5$ to $R_7$ decreases, plasticization efficiency, volatile loss, an elongation rate, and an absorption rate are excellent. However, Examples 4 and 5 show aspects different from Examples 6 to 9, which was attributed to the characteristics of tributylcitrate. In addition, referring to Examples 11 to 14, it can be seen that as the content of the cyclohexane-1,4-diester-based substance decreases, migration loss, volatile loss, an elongation rate, and an absorption rate are improved.

On the other hand, it can be seen that Comparative Example 1 including only a cyclohexane-1,4-diester-based substance exhibited significantly low heat resistance compared to Examples, Comparative Example 2 not including a citrate-based substance exhibited significantly low tensile strength compared to Examples, Comparative Example 3 not including an epoxidized alkyl ester composition exhibited significantly low heat resistance compared to Examples, Comparative Example 4 including dibutyl cyclohexane-1,4-dicarboxylate exhibited significantly degraded properties in terms of migration loss and volatile loss compared to Examples, Comparative Example 5 including diisodecyl cyclohexane-1,4-dicarboxylate exhibited significantly degraded properties in terms of plasticization efficiency and an absorption rate compared to Examples, Comparative Example 6 not including a cyclohexane-1,4-diester-based substance exhibited significantly degraded properties in terms of migration loss, volatile loss, tensile strength, an elongation rate, and heat resistance compared to Examples, Comparative Example 7 including dibutyl cyclohexane-1,4-dicarboxylate and not including a citrate-based substance exhibited degraded properties in terms of migration loss, volatile loss, tensile strength, and an elongation rate compared to Examples, Comparative Example 8 including diisodecyl cyclohexane-1,4-dicarboxylate and not including a citrate-based substance exhibited degraded plasticization efficiency and a significantly low elongation rate and a significantly low absorption rate compared to Examples, and Comparative Example 9 including acetyl tributyl citrate exhibited low heat resistance compared to Examples.

The invention claimed is:

1. A plasticizer composition comprising:
    a cyclohexane-1,4-diester-based substance of the following Chemical Formula 1;
    an epoxidized alkyl ester composition comprising one or more compounds of the following Chemical Formula 2; and
    a citrate-based substance of the following Chemical Formula 3:

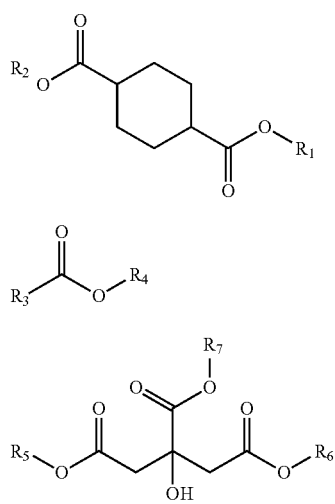

Chemical Formula 1

Chemical Formula 2

Chemical Formula 3 wherein in Chemical Formula 1 to Chemical Formula 3:
$R_1$ and $R_2$ each independently are a C8 alkyl group;
$R_3$ is a C8 to C20 alkyl group comprising one or more epoxy groups; and
$R_4$ to $R_7$ each independently are a C4 to C10 alkyl group, and wherein the sum of the number of carbon atoms of the alkyl group of $R_4$ and the average number of carbon atoms of the alkyl groups of $R_5$ to $R_7$ ranges from 10 to 15, and wherein the plasticizer composition comprises, with respect to a total weight thereof:
    10 to 90 wt % of the cyclohexane-1,4-diester-based substance;
    5 to 70 wt % of the epoxidized alkyl ester composition; and
    5 to 70 wt % of the citrate-based substance.

2. The plasticizer composition of claim 1, wherein the $R_1$ and $R_2$ each independently are any one selected from the group consisting of an n-octyl group, an isooctyl group, and a 2-ethylhexyl group.

3. The plasticizer composition of claim 1, wherein the epoxidized alkyl ester composition has an iodine value of less than 3.5 $I_2$ g/100 g.

4. The plasticizer composition of claim 1, wherein the epoxidized alkyl ester composition has an oxirane content (O.C.) of 3.5% or more.

5. The plasticizer composition of claim 1, wherein the $R_4$ is selected from the group consisting of a butyl group, an isobutyl group, a pentyl group, an isopentyl group, a hexyl group, an isohexyl group, a 2-ethylhexyl group, an octyl group, an isononyl group, a decyl group, an isodecyl group, and a 2-propylheptyl group.

6. The plasticizer composition of claim 1, wherein the $R_5$ to $R_7$ each independently are a C4 to C8 alkyl group.

7. The plasticizer composition of claim 1, wherein the $R_5$ to $R_7$ each independently are a C5 to C10 alkyl group.

8. The plasticizer composition of claim 1, wherein the $R_5$ to $R_7$ each independently are any one selected from the group consisting of an n-butyl group, an isobutyl group, an n-pentyl group, an isopentyl group, an n-hexyl group, an isohexyl group, an n-heptyl group, an isoheptyl group, an n-octyl group, an isooctyl group, a 2-ethylhexyl group, an n-nonyl group, an isononyl group, a 2-propylheptyl group, and an isodecyl group.

9. The plasticizer composition of claim 1, wherein the epoxidized alkyl ester composition further includes a saturated fatty acid alkyl ester composition including one or more compounds of the following Chemical Formula 4:

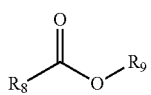

Chemical Formula 4 wherein in Chemical Formula 4:
$R_8$ is a C8 to C20 alkyl group; and
$R_9$ is a C4 to C10 alkyl group.

10. A resin composition comprising:
    a resin in an amount of 100 parts by weight; and
    the plasticizer composition of claim 1 in an amount of 5 to 150 parts by weight.

11. The resin composition of claim 10, wherein the resin is one or more selected from the group consisting of a straight vinyl chloride polymer, a paste vinyl chloride polymer, an ethylene-vinyl acetate copolymer, an ethylene polymer, a propylene polymer, polyketone, polystyrene, polyurethane, natural rubber, synthetic rubber, and a thermoplastic elastomer.

* * * * *